United States Patent [19]

McCoy

[11] Patent Number: 4,466,428
[45] Date of Patent: Aug. 21, 1984

[54] PATELLA SUPPORT APPARATUS

[76] Inventor: Dalton R. McCoy, No. 14 Birchwood Pl., Kearney, Buffalo County, Nebr. 68847

[21] Appl. No.: 398,738

[22] Filed: Jul. 16, 1982

[51] Int. Cl.³ .............................................. A61F 3/00
[52] U.S. Cl. ................................................... 128/80 C
[58] Field of Search ................... 128/80 C, 165, 87 R; 2/22, 24

[56] References Cited

U.S. PATENT DOCUMENTS

| | | | |
|---|---|---|---|
| 1,388,772 | 8/1921 | Sheehan | 128/165 |
| 2,179,903 | 11/1939 | Spears | 128/80 C |
| 2,270,685 | 1/1942 | Miller | 128/165 |
| 3,194,233 | 7/1965 | Peckham | 128/80 C |
| 3,473,527 | 10/1969 | Spiro | 128/80 C |
| 3,853,123 | 12/1974 | Moore | 128/80 C |
| 4,084,584 | 4/1978 | Detty | 128/80 C |
| 4,250,578 | 2/1981 | Barlow | 2/24 |
| 4,287,885 | 9/1981 | Applegate | 128/80 C |
| 4,296,744 | 10/1981 | Palumbo | 128/165 X |

FOREIGN PATENT DOCUMENTS 794292 2/1936 France .............................. 128/80 C Primary Examiner—John D. Yasko
Attorney, Agent, or Firm—Henderson & Sturm

[57] ABSTRACT

A patella support apparatus having a brace member (13) for positioning about the patella (25) and for preventing lateral or medial movements thereof, and a popliteal member (12) for affixing the brace member (13) in place.

1 Claim, 4 Drawing Figures

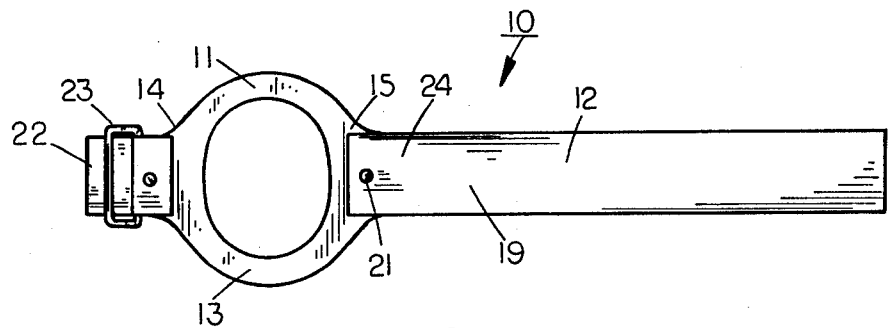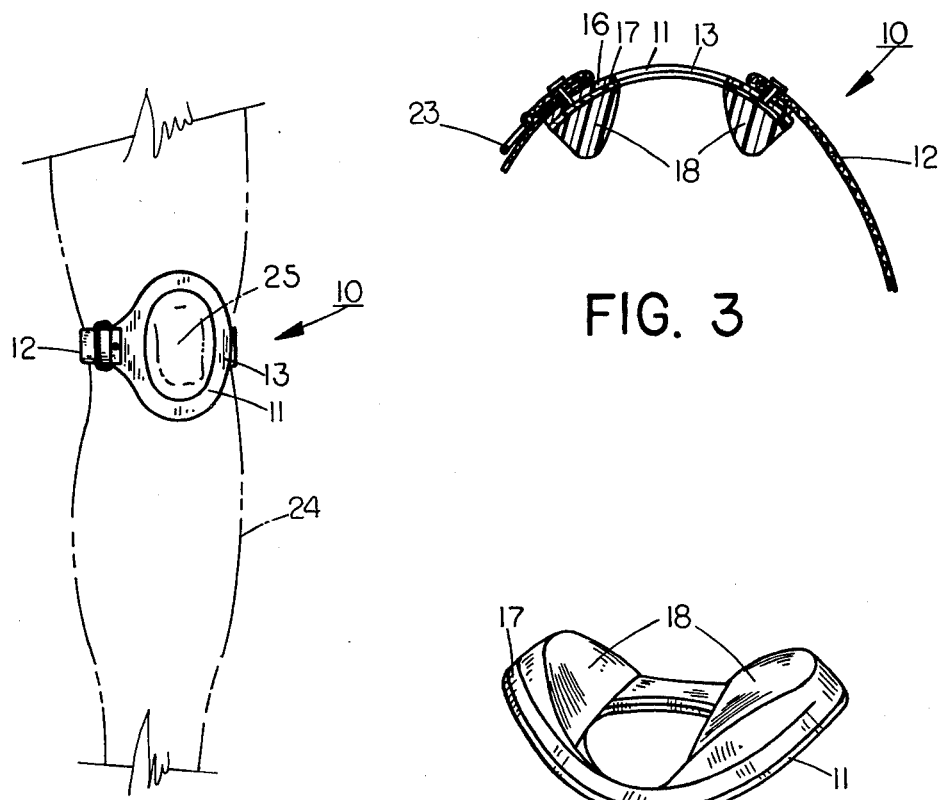

PATELLA SUPPORT APPARATUS

TECHNICAL FIELD

This invention relates generally to patella support structures.

BACKGROUND ART

The patella comprises a flat, triangular-shaped bone located at the anterior portion of the knee joint. Commonly regarded as a sesamoid bone, the patella serves to protect the front of the joint, and increases the leverage of the quadriceps extensor by making it act at a greater angle. The patella attaches to four muscles, namely: the rectus, crureus, vastus internus and the vastus externus.

A great variety of leg traumas necessitate limiting the mobility of the patella in order to effectuate the healing process. To accomplish this, many knee braces and the like are found in the prior art.

For instance, braces or casts that prevent movement of the leg vis-a-vis the knee have been used. So constrained, the patella will not move during the healing period. Often times, however, the extent of the injury does not warrant such a lengthy, uncomfortable and inconvenient incapacitation of movement.

To avoid the use of general leg constraints, many prior art devices utilize an elastic or resilient sleeve-like structure for disposition about the knee area, as well as portions of the leg located proximal thereto. Some of these sleeves includes pads attached thereto for disposition about the patella in an attempt to provide additional support.

While these devices are suitable in some instances, they have not been all together successful in adequately preventing lateral and medial movement of the patella. Even the use of pads or other support fixtures about the patella have not been wholly satisfactory because the pads are connected to the sleeve, and the sleeve may stretch with movement of the leg.

Therefore, while the sleeve-like structures will not substantially impair the user's ability to walk, run or jump, as do the whole leg brace or cast, the sleeve-like structures do not adequately prevent lateral and medial movement of the patella during these same activities.

Finally, such injuries may be resolved through radical surgery followed by a long convalescent period. Such an alternative has obvious drawbacks and will normally be resorted to only in an extreme case.

A need therefore exists for a patella support apparatus that will prevent lateral and medial movement of the patella while walking, running or jumping without substantially impairing the user's ability to walk, run or jump.

DISCLOSURE OF INVENTION

These problems and others are resolved by the provision of a patella support apparatus having a brace member and a popliteal member.

The brace member may be comprised of an annularly shaped support member formed of prolypropylene thermoplastic material. The support member may be inwardly curved across its lateral diameter to result in a pre-curved shape to facilitate disposition of the brace member about the patella.

A pad member may be connected to the posterior side of the support member. The pad member may be a polyethylene material of firm density, such as Pe-lite non-allergenic foam. Such a pad should be shaped to have a larger cross section on opposing sides such that the pad material will provide sufficient support on either side of the patella.

The popliteal member may be a strap of cotton webbing connected on one side of the annularly shaped support member. A fastening member may be connected to the opposing side of the annularly shaped support member. This fastening member may include a short section of cotton webbing that attaches a metal loop thereto.

To use the patella support apparatus, the patient positions the brace member such that the patella becomes disposed within the annularly shaped support member. The popliteal member may then be disposed around the leg. The strap may then be fastened to the opposing side of the support member by appropriate use of the loop provided therefor.

Properly positioned and fastened in place, this patella support apparatus will not substantially impair the user's ability to walk, run or jump. Just as importantly, the patella support apparatus will substantially prevent lateral and medial movement of the patella, thereby furthering healing and preventing further injury to the protected area.

BRIEF DESCRIPTION OF THE DRAWINGS

These and other attributes of the instant invention will become more clear upon a thorough review of the following description of the best mode for carrying out the invention, particularly when reviewed in conjunction with the drawings, wherein:

FIG. 1 is a perspective view of the patella support apparatus as positioned upon a leg;

FIG. 2 is a front elevational view of the patella support apparatus;

FIG. 3 is a top plan enlarged sectional view of the patella support apparatus; and FIG. 4 is an enlarged perspective view of the brace member.

BEST MODE FOR CARRYING OUT THE INVENTION

Referring now to the drawings, and in particular to FIG. 2, the apparatus may be seen as denoted generally by the numeral 10. The apparatus (10) includes more particularly a brace member (11) and a popliteal member (12). These members (11 and 12) will now be described in more detail.

The brace member (11) may be comprised of a substantially annularly-shaped support member (13). The annularly-shaped support member (13) includes two flange members (14 and 15) disposed opposite one another along the support member's (13) lateral diameter. These flanges (14 and 15) facilitate attachment of the popliteal member (12) as will be described below.

The annularly-shaped support member (13) may be concavely shaped as depicted in FIG. 3 to facilitate attachment of the apparatus (10) to a leg. The support member (13) may be comprised of one, two or more layers of material as desired. In FIG. 3, the applicant discloses the support member (13) as being comprised of one layer (16).

A pad member (17) having a periphery substantially equal with that of the support member (13) and having a patella opening disposed therethrough may be attached to the underside thereof. In addition, two other pad members (18) may be attached to the first pad member (17) on either side of the patella opening. These additional pads (18) are shaped somewhat like an orange section as shown and provide support for the patella as will be appreciated more fully below.

The popliteal member (12) includes a strap (19) affixed by a rivet (21) or other suitable fastening member to one side of the support member (13). More particularly, the strap (19) attaches to a flange member (15). The remaining flange member (14) may have a fastening member (21) attached thereto, again by a rivet or other appropriate fastening mechanism. The fastening member (21) includes a small section of strap (22) and a metal loop (23) disposed therein as depicted in FIG. 3. It will be appreciated that the strap (19) and the fastening member (21) may be operably interwoven to achieve attachment of the two.

If desired, a small section of elastic material (24) may be added to the strap (19) to provide additional comfort to the wearer.

Referring now to FIG. 1, a section of a human leg has been depicted in phantom lines as denoted by the numeral 24. As shown, the annularly-shaped support member (13) and the pad members (17 and 18) affixed thereto may be disposed about the patella (25) such that the patella (25) extends through the opening of the support member (13). The brace member (13) may then be affixed in place by positioning the popliteal member (12) behind the leg and operably engaging the strap (19) with the fastening member (21).

It will be appreciated that this apparatus (10) substantially prevents lateral and medial movement of the patella while walking, running or jumping without substantially impairing the user's ability to walk, run or jump. The apparatus may be manufactured at a modest cost and a single size will accomodate many different sized users. The apparatus (10) presents no particular sanitation problems and may be emplaced or removed with ease.

Obviously, many modifications and variations of the present invention are possible in light of the above teachings. It is therefore to be understood that, within the scope of the appended Claims, the invention may be practised otherwise than as specifically described.

I claim:

1. A patella support apparatus comprising:
   (a) a brace means substantially rigidly encircling the patella, for applying pressure substantially completely around and to the patella, said brace means including a substantially annular support member concavely shaped to facilitate the positioning of the said brace means about the patella, said support member having a pair of spaced apart projections operably integrally disposed thereon, said projections being thicker on the outside portion thereof than on the inside portion thereof whereby said projections will apply pressure to the outer and inner portions of the patella and pad means integrally disposed on said support member continuously between the top and bottom of said projections for applying pressure to the top and bottom of the patella; and
   (b) a popliteal member comprising a strap and being affixable to said brace member to secure said brace means in position about the patella such that said brace means substantially prevents lateral and medial movement of the patella while walking, running or jumping without substantially impairing the user's ability to walk, run or jump.

* * * * *